(12) United States Patent
Wiest et al.

(10) Patent No.: US 9,333,222 B2
(45) Date of Patent: May 10, 2016

(54) HISTONE DEACETYLASE INHIBITORS AS THERAPEUTIC AGENTS FOR NIEMANN-PICK TYPE C DISEASE

(75) Inventors: Olaf Wiest, South Bend, IN (US); Frederick R. Maxfield, Chappaqua, NY (US); Paul Helquist, Granger, IN (US)

(73) Assignees: University of Notre Dame du Lac, Notre Dame, IN (US); Cornell University, Ithaca, NY (US)

( * ) Notice: Subject to any disclaimer, the term of this patent is extended or adjusted under 35 U.S.C. 154(b) by 544 days.

(21) Appl. No.: 12/888,267

(22) Filed: Sep. 22, 2010

(65) Prior Publication Data

US 2011/0071109 A1 Mar. 24, 2011

Related U.S. Application Data

(63) Continuation-in-part of application No. PCT/US2010/036550, filed on May 28, 2010.

(60) Provisional application No. 61/181,996, filed on May 28, 2009.

(51) Int. Cl.
*A61K 31/165* (2006.01)
*A61K 31/4045* (2006.01)
*A61K 31/724* (2006.01)
*A61K 31/721* (2006.01)
*A61K 47/48* (2006.01)

(52) U.S. Cl.
CPC .............. *A61K 31/724* (2013.01); *A61K 31/165* (2013.01); *A61K 31/4045* (2013.01); *A61K 31/721* (2013.01); *A61K 47/48092* (2013.01)

(58) Field of Classification Search
None
See application file for complete search history.

(56) References Cited

U.S. PATENT DOCUMENTS

| 4,946,999 | A | 8/1990 | Koseki et al. | |
|---|---|---|---|---|
| 5,710,268 | A | 1/1998 | Wimmer | |
| 7,235,688 | B1 * | 6/2007 | Helquist et al. | 562/452 |
| 7,705,017 | B2 | 4/2010 | Cummings et al. | |
| 2002/0151523 | A1 | 10/2002 | Davis et al. | |
| 2011/0237832 | A1 | 9/2011 | Helquist | |

FOREIGN PATENT DOCUMENTS

| CN | 1939898 | 4/2007 |
|---|---|---|
| WO | 0249676 A2 | 6/2002 |
| WO | 2004022099 A2 | 3/2004 |
| WO | WO 2010/138802 A2 * | 12/2010 |

OTHER PUBLICATIONS

Xiong et al., World Journal of Pediatrics, (Feb. 2012), 8(1), pp. 61-66 (Abstract).*
Gottlicher, Annals of Hematology, Feb. 2004, vol. 83, Issue 1 Supplement, pp. S91-S92.*
Chang et al., The Journal of Biological Chemistry, 2005, vol. 280 (22), pp. 20917-20920.*
Patterson et al., Lancet Neurology, Sep. 2007, vol. 6(9), pp. 765-772; only Abstract provided.*
Dokmanovic et al., Molecular Cancer Research, 2007, vol. 5, pp. 981-989.*
Kim, Sun-Jung et al., "Defective Cholesterol Traffic and Neuronal Differentiation in Neural Stem Cells of Niemann-Pick type C Disease Improved by Valproic Acid, a Histone Deacetylase Inhibitor," Biochemical and Biophysical Research Communications, 2007, vol. 360, pp. 593-599.
Araki, Hiroto et al., "Expansion of Human Umbilical Cord Blood SCID-Repopulating Cells Using Chromatin-Modifying Agents," Experimental Hematology, 2006, vol. 34, pp. 140-149.
Atadja, Peter, "Development of the Pan-DAC Inhibitor Panobinostat (LBH589): Successes and Challenges," Cancer Letters, 2009, vol. 280, pp. 233-241.
Tan, Jiahuai et al., "Novel Histone Deacetylase Inhibitors in Clinical Trials as Anti-Cancer Agents," Journal of Hematologty & Oncology, 2010, vol. 3, No. 5, pp. 2-13.
Garbes, Lutz et al., "LBH589 Induces up to 10-fold SMN Protein Levels by Several Independent Mechanisms and is Effective Even in Cells From SMA Patients Non-Responsive to Valproate," Human Molecular Genetics, 2009, vol. 18, No. 19, pp. 3645-3658.
Bradner, James E. et al., "Chemical Genetic Strategy Identifies Histone Deacetylase 1 (HDAC1) and HDAC2 as Therapeutic Targets in Sickle Cell Disease," PNAS, Jul. 13, 2010, vol. 107 No. 28, pp. 12617-12622.
Gevry, Nicholas Y. et al., "Regulation of Niemann-Pick C1 Gene Expression by the 3'5'-Cyclic Adenosine Monophosphate Pathway in Steroidogenic Cells," Molecular Endocrinology, 2003, vol. 17, pp. 704-715.
Davie, James R., "Inhibition of Histone Deacetylase Activity by Butyrate," The American Society for Nutritional Sciences J. Nutr., Jul. 2003, vol. 133, pp. 2485S-2493S.
Chatterjee, Anamitra et al., "An Efficient Synthesis of (+)-Trichostatic Acid and Analogues: A New Route to (+)- Trichostatin A," Organic Letters, 2010, vol. 12, No. 4, pp. 832-834.
Moorlag, Henk et al., "Pig Liver Esterase Catalyzed Hydrolyses of Racemic a-Substituted a-Hydroxy Esters," J. Org. Chem., 1990, vol. 55, pp. 5878-5881.
Nicolaou, K.C. et al., "A Mild and Selective Method for the Hydrolysis of Esters with Trimethyltin Hydroxide," Agnew Chem. Int Ed. 2005, vol. 44, pp. 1378-1382.
Lee-Ruff, E., et al., Oxidation of Allyl and Benzyl Ethers by 2,3-dichloro-5,6-dicyanobenzoquinone (DDQ), Can J. Chem, 1989, vol. 67, pp. 699-702.

(Continued)

*Primary Examiner* — Savitha Rao
*Assistant Examiner* — Gregg Polansky
(74) *Attorney, Agent, or Firm* — Schwabe Williamson & Wyatt

(57) ABSTRACT

Embodiments herein relate to the field of lysosomal storage disorders, and, more specifically, to methods of treating lysosomal storage disorders such as Niemann-Pick type C disease, for instance with inhibitors of histone deacetylases, particularly inhibitors of class 1 histone deacetylases. In various embodiments, methods of treating Niemann-Pick type C disease with inhibitors of class 1 histone deacetylases are described.

10 Claims, 11 Drawing Sheets

(56) References Cited

OTHER PUBLICATIONS

Kobayashi, Yusuke et al., "Asymmetric Synthetic Study of Macrolactin Analogues," Tetrahedron, 2005, vol. 61, pp. 2607-2622.
Handa, Masaki et al., "Studies on the Synthesis of Apoptolidin A. 1. Synthesis of the C(1)-C(11) Fragment," J. Org. Chem., 2008, vol. 73, pp. 1031-1035.
Marshall, James A. et al., "Formation of Transient Chiral Allenylindium Reagents from Enantioenriched Propargylic Mesylates through Oxidative Transmetalation. Applications to the Synthesis of Enantioenriched Homopropargylic Alcohols," J. Org. Chem., 1999, vol. 64, pp. 696-697.
Yue, Dawei et al., "Synthesis of 2,3-Disubstituted Benzo[b]thiophenes via Palladium-Catalyzed Coupling and Electrophilic Cyclization of Terminal Acetylenes," J. Org. Chem., 2002, vol. 67, pp. 1905-1909.
Larsen, Catharine H. et al., "Palladium-Catalyzed Heck Alkynylation of Benzyl Chlorides," Synlett, 2006, No. 18, pp. 2941-2946.
Charrier, Cedric et al., "Biological Activities of Subsituted Trichostatic Acid Derivatives," J. Chem. Sci., 2009, vol. 121, No. 4, pp. 471-479.
Huang, Jinkun et al., "Palladium-Catalyzed a-Vinylation of Carbonyl Compounds," Organic Letters, 2007, vol. 9, No. 21, pp. 4343-4346.
Zhao, Xi et al., "A New Synthetic Method of Natural Product Trichostatin A," Chin J. Org. Chem., 2007, vol. 27, No. 12, pp. 1509-1515.
Zhang, Shilei, et al., "Efficient, Enantioselective Organocatalytic Synthesis of Trichostatin A," Adv. Synth. Catal., 2006, vol. 348, pp. 1228-1234.
Mori, Kenji, et al., "Synthesis of Trichostatin A, a Potent Differentiation Inducer of Friend Leukemic Cells, and its Antipode,"Tetrahedron, 1988, vol. 44, No. 19, pp. 6013-6020.
Fleming, Ian, et al., "The Total Synthesis of (+/−)-Trichostatin A," Tetrahedron, 1983, vol. 39, No. 6, pp. 841-846.
Chieffi, Andre, et al., "Catalytic Asymmetric Vinylation of Ketone Enoates," Organic Letters, 2001, vol. 3, No. 12, pp. 1897-1900.
Marshall, James A., et al., "(R)- and (S)-4-TIPS-3-butyn-2-ol. Useful Precursors of Chiral Allenylzinc and Indium Reagents," J. Org. Chem., 2006, vol. 71, pp. 4840-4844.
Taylor, A.M. et al., "Palladium-Catalyzed Enantioselective Alpha-Arylation and Alpha-Vinylation of Oxindoles Facilitated by an Axially Chiral P-Stereogenic Ligand," J. Am. Chem Soc., 2009, vol. 131, pp. 9900-9901.
Bradner, James E. et al., "Chemical Phylogenetics of Histone Deacetylases," Nat Chem Biol., 2010, vol. 6, No. 3, pp. 238-243.
Bradner, James E. et al., "Supplementary Information for Chemical; Phylogenetics of Histone Deacetylases," Nat Chem Biol., 2010, vol. 6, No. 3, pp. 1-26.
Eyal, Sara et al., "The Activity of Antiepileptic Drugs as Histone Deacetylase Inhibitors," Epilepsia, 2004, vol. 45, No. 7, pp. 737-744.
Gregoretti, Ivan V. et al., "Molecular Evolution of the Histone Deacetylase Family: Functional Implications of Phylogenetic Analysis," J. Mol. Biol., 2004, vol. 338, pp. 17-31.
Vanier, Marie T., "Niemann-Pick Disease Type C," Orphanet Journal of Rare Diseases, 2010, vol. 5, No. 16, pp. 1-18.

* cited by examiner

Figure 5

HISTONE DEACETYLASE INHIBITORS AS THERAPEUTIC AGENTS FOR NIEMANN-PICK TYPE C DISEASE

CROSS REFERENCE TO RELATED APPLICATIONS

The present application is a continuation-in-part of and claims priority to PCT Application No. PCT/US2010/036550, filed on May 28, 2010, entitled "COMPOSITIONS AND THEIR USE FOR REMOVING CHOLESTEROL," which claimed priority to U.S. Provisional Patent Application No. 61/181,996, filed May 28, 2009, entitled "COMPOSITIONS AND THEIR USE FOR REMOVING CHOLESTEROL." The entire disclosures of both applications are hereby incorporated by reference in their entirety.

TECHNICAL FIELD

Embodiments herein relate to the field of lysosomal storage disorders, and, more specifically, to methods of treating lysosomal storage disorders such as Niemann-Pick type C disease, with inhibitors of histone deacetylases, particularly inhibitors of class 1 histone deacetylases.

BACKGROUND

Niemann-Pick type C disease (NPC) is a fatal neurodegenerative lysosomal storage disorder resulting in abnormal accumulation of unesterified cholesterol, glycosphingolipids, bis(monoacyl glycerol) phosphate, and other lipids in late endosome/lysosomes (LE/Ly) of many cell types. Two genes, NPC1 and NPC2, have been linked to the NPC defect in humans, and the precise mechanisms of action of these proteins are still under investigation. The incidence is estimated between 1:120,000 and 1:50,000 live births.

Treatment options for NPC are limited. The only drug approved for the treatment of NPC in Europe is Zavesca (Miglustat), which inhibits glycosphingolipid synthesis. This treatment has been shown to stabilize the disease progression, but does not reverse the damaged neurons or promote recovery of lost neurons.

BRIEF DESCRIPTION OF THE DRAWINGS

Embodiments will be readily understood by the following detailed description in conjunction with the accompanying drawings. Embodiments are illustrated by way of example and not by way of limitation in the figures of the accompanying drawings.

FIG. 2A shows wild-type human fibroblast GM5659 cells, FIG. 2B shows NPC1 human fibroblast GM03123 cells, FIG. 2C shows NPC1 human fibroblast GM03123 cells after 48 hours of treatment with 37 nM LBH-589, and FIG. 2D shows NPC1 human fibroblast GM03123 cells after 48 hours of treatment with 111 nM TSA, in accordance with various embodiments;

FIG. 5 is a digital image showing the effect of HDACi on NPC1 expression by Western blot analysis, in accordance with various embodiments;

DETAILED DESCRIPTION OF DISCLOSED EMBODIMENTS

Figure 1:
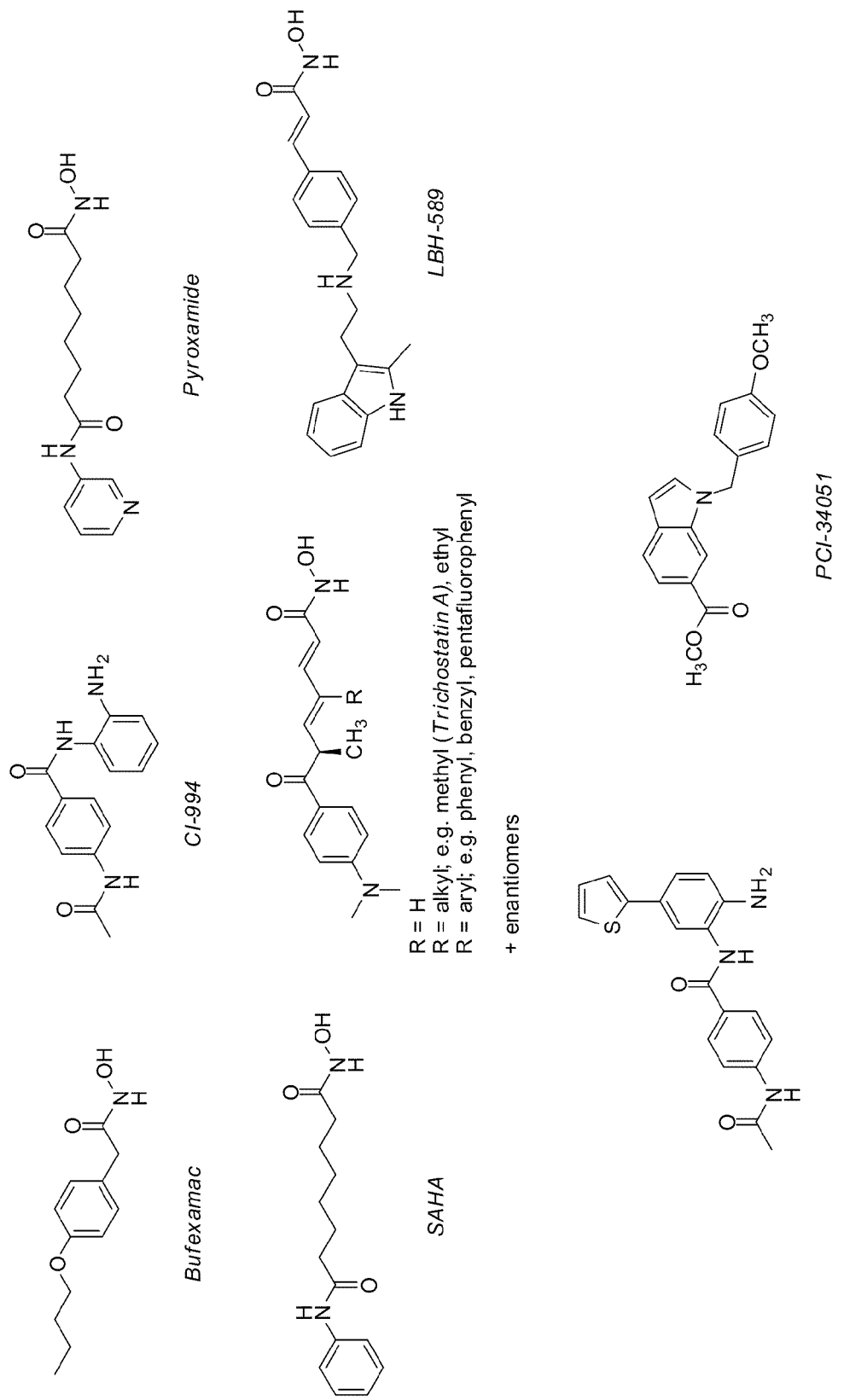
FIG. 1 illustrates the chemical structures of various histone deacetylase inhibitors (HDACi), in accordance with various embodiments.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous.

In various embodiments, methods and compositions for the treatment of lysosomal storage disorders are provided. Certain embodiments are directed at treating lysosomal storage disorders, for instance Niemann-Pick type C disease (NPC), with histone deacetylase inhibitors (HDACi), for instance an HDACi that preferentially inhibits or is specific to class 1 histone deacetylases (HDACs).

As used herein, the term "lysosomal storage disorder" or "LSD" includes a group of approximately 40 rare inherited metabolic disorders that result from defects in lysosomal function. The defects in lysosomal function generally are a consequence of a deficiency of a single enzyme required for the metabolism of lipids, glycoproteins, or mucopolysaccharides. Individually, LSDs occur with incidences of less than 1:100,000, however, as a group the incidence is about 1:5,000-1:10,000. LSDs generally affect children, often causing death within a few months or years of birth.

One specific, non-limiting example of an LSD is NPC, an LSD associated with mutations in NPC1 or NPC2 genes. In NPC, the protein product of the NPC1 gene is not an enzyme, but a transporter in the endosomal-lysosomal system, which moves large water-insoluble molecules through the cell. The protein coded by the NPC2 gene acts in cooperation with the NPC1 protein in transporting molecules in the cell. The disruption of this transport system results in the accumulation of cholesterol and glycolipids in lysosomes.

Other specific, non-limiting examples of LSDs include activator deficiency/GM2 gangliosidosis, alpha-mannosidosis, aspartylglucosaminuria, cholesteryl ester storage disease, chronic hexosaminidase A deficiency, cystinosis, Danon disease, Fabry disease, Farber disease, fucosidosis, galactosialidosis, Gaucher disease (types I-III), GM1 gangliosidosis, I-cell disease/mucolipidosis II, infantile free sialic acid storage disease/ISSD, juvenile hexosaminidase A deficiency, Krabbe disease, metachromatic leukodystrophy, mucopolysaccharidoses disorders, pseudo-Hurler polydystrophy/mucolipidosis IIIA, MPSI Hurler syndrome, MPSI Scheie syndrome, MPS I Hurler-Scheie syndrome, MPS II Hunter syndrome, Sanfilippo syndrome, Morquio syndrome, MPS IX hyaluronidase deficiency, MPS VI Maroteaux-Lamy, MPS VII Sly syndrome, mucolipidosis I/sialidosis, multiple sulfatase deficiency, neuronal ceroid lipofuscinoses, Pompe disease, pycnodysostosis, Sandhoff disease, Schindler disease, Salla disease, Tay-Sachs, and Wolman disease.

Methods of treating LSDs, such as NPC, with HDACi are provided herein in various embodiments. As used herein, the term "histone deacetylase" or "HDAC" refers to a class of enzymes that have various functions in epigenetic regulation of gene expression. One such function exhibited by some HDACs is the removal of acetyl groups from an ε-N-acetyl lysine amino acid on a histone. HDAC proteins may be grouped into four classes (see Table 1, below) based on function and DNA sequence similarity. The first two classes are considered "classical" HDACs whose activities are inhibited by trichostatin A (TSA), whereas the third class is a family of $NAD^+$-dependent proteins not affected by TSA and phylogenetically not related to the other three classes. The fourth class is considered an atypical category, based on DNA sequence similarity to the others. Class II is further subdivided into two subclasses: Class IIA and Class IIB, the later of which is comprised of two independent HDAC domains.

TABLE 1

Classes of Histone Deacetylases (HDACs) and classification of human HDACS

| Class I | Class IIA | Class IIB | Class III | Class IV |
|---------|-----------|-----------|-----------|----------|
| HDAC1 | HDAC4 | HDAC6 | Sirtuin1 (SIRT1) | HDAC11 |
| HDAC2 | HDAC5 | HDAC10 | SIRT2 | |
| HDAC3 | HDAC9 | | SIRT3 | |
| HDAC8 | HDAC7 | | SIRT4 | |
| | | | SIRT5 | |
| | | | SIRT6 | |
| | | | SIRT7 | |

A number of inhibitors of HDACs (HDACi) have been identified that act on class I, IIa and IIb HDACs, typically by binding to the zinc-containing catalytic domain of the HDACs. These classical HDACi fall into several groupings, in approximate order of decreasing potency, as shown in Table 2. Second-generation HDACi derived from these groupings include the hydroxamic acids vorinostat (SAHA), belinostat (PXD101), LAQ824, panobinostat (LBH-589), givinostat (ITF2357), and the benzamides entinostat (MS275), CL-994, and mocetinostat (MGCD0103). Generally, benzamides inhibit class I, but not class II HDACs, and hydroxamic acids are stronger inhibitors of class I and IIb HDACs than of class IIa HDACs, while isoform selectivity within a class is significantly lower.

TABLE 2

Classical HDACi

| 1 | hydroxamic acids, such as trichostatin A |
| 2 | cyclic tetrapeptides (such as trapoxin B), and the depsipeptides |
| 3 | Benzamides |
| 4 | electrophilic ketones |
| 5 | aliphatic acid compounds such as phenylbutyrate and valproic acid |

In accordance with embodiments herein, FIG. 1 shows a collection of various HDACi that were synthesized or obtained from commercial sources and which have varying chemotypes, potencies, and selectivities: the weak HDACi Bufexamac, the medium activity benzamide CL-994, and the FDA-approved hydroxamic acid SAHA and its analog, pyroxamide, and the potent hydroxamic acids LBH-589 and trichostatin A (TSA) and analogs thereof, as well as two isoform-selective HDACi, thiophene benzamide and PCI-34051.

Figure 2:
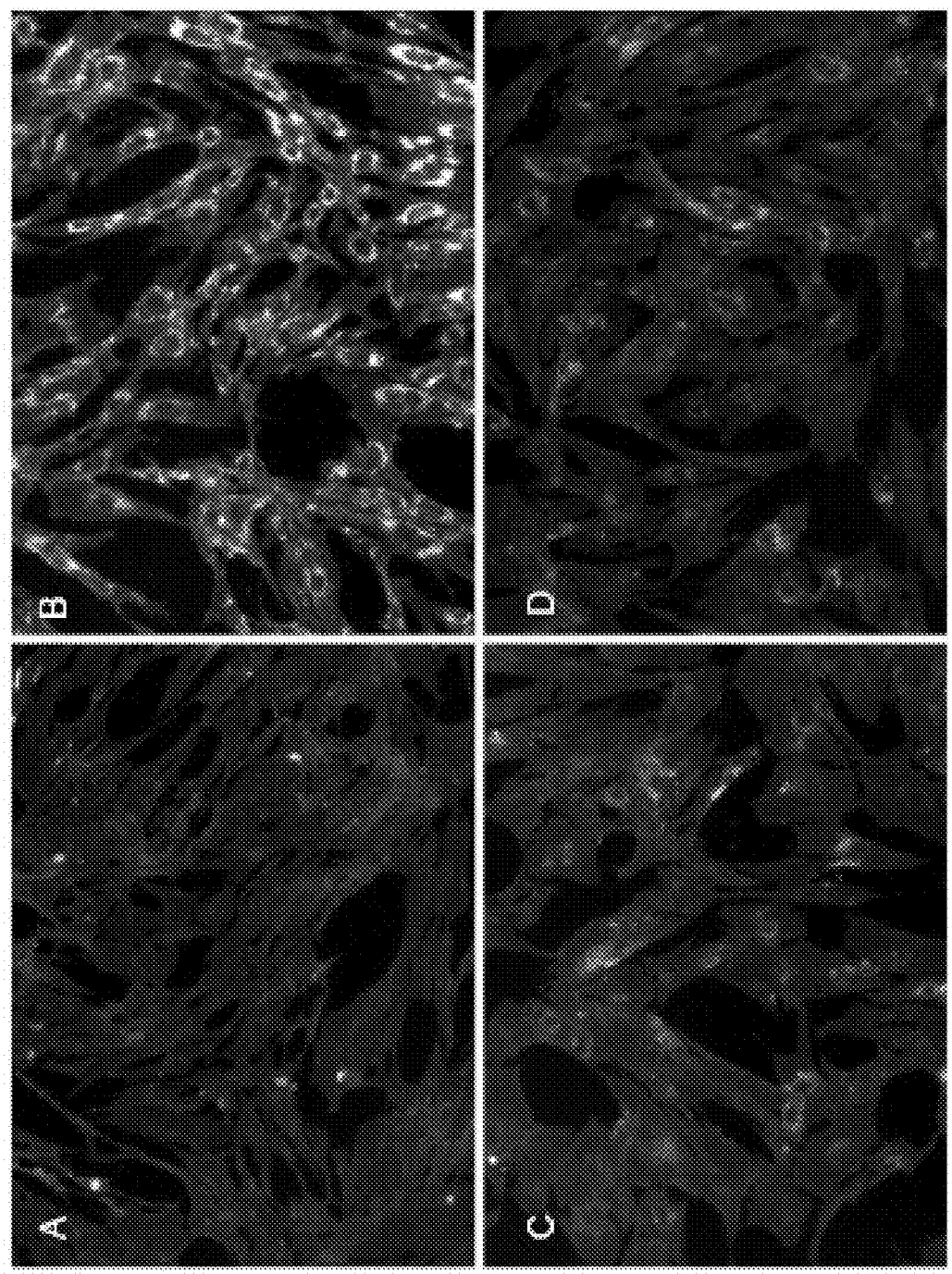
FIGS. 2A-2D illustrate representative filipin images of HDACi treated NPC1 fibroblasts.

As shown in FIG. 2, heterozygous human NPC1 fibroblasts (GM03123) defective in both alleles of NPC1 were initially treated with HDACi at various concentrations and analyzed using a microscopy-based assay to estimate the free cholesterol in lysosomal storage organelles (LSO) in NPC1 fibroblasts. Briefly, NPC1 human fibroblasts GM03123 were treated with HDACi 37 nM LBH-589 or 111 nM TSA and incubated for 48 hours. Cells were subsequently fixed with 2% PFA and stained with filipin. Images were acquired with wide-field microscopy at 10× magnification. Representative images of filipin-stained wild-type (WT) cells (GM5659; FIG. 2A) indicated no significant accumulation of free cholesterol in the LSO. Filipin staining of NPC1 human fibroblast GM03123, treated with the vehicle control DMSO (FIG. 2B), clearly showed extensive accumulation of free cholesterol in the LSOs of the cells. Significantly, the treatment of NPC1 human fibroblast GM03123 cells with either the HDACi LBH-589 (37 nM, FIG. 2C) or TSA (111 nM, FIG. 2D) resulted in dramatic correction of the NPC1 phenotype as observed by reduced filipin staining in the LSOs of the cells. These HDACi-treated NPC1 cells were comparable to the WT human fibroblasts.

Figure 3:
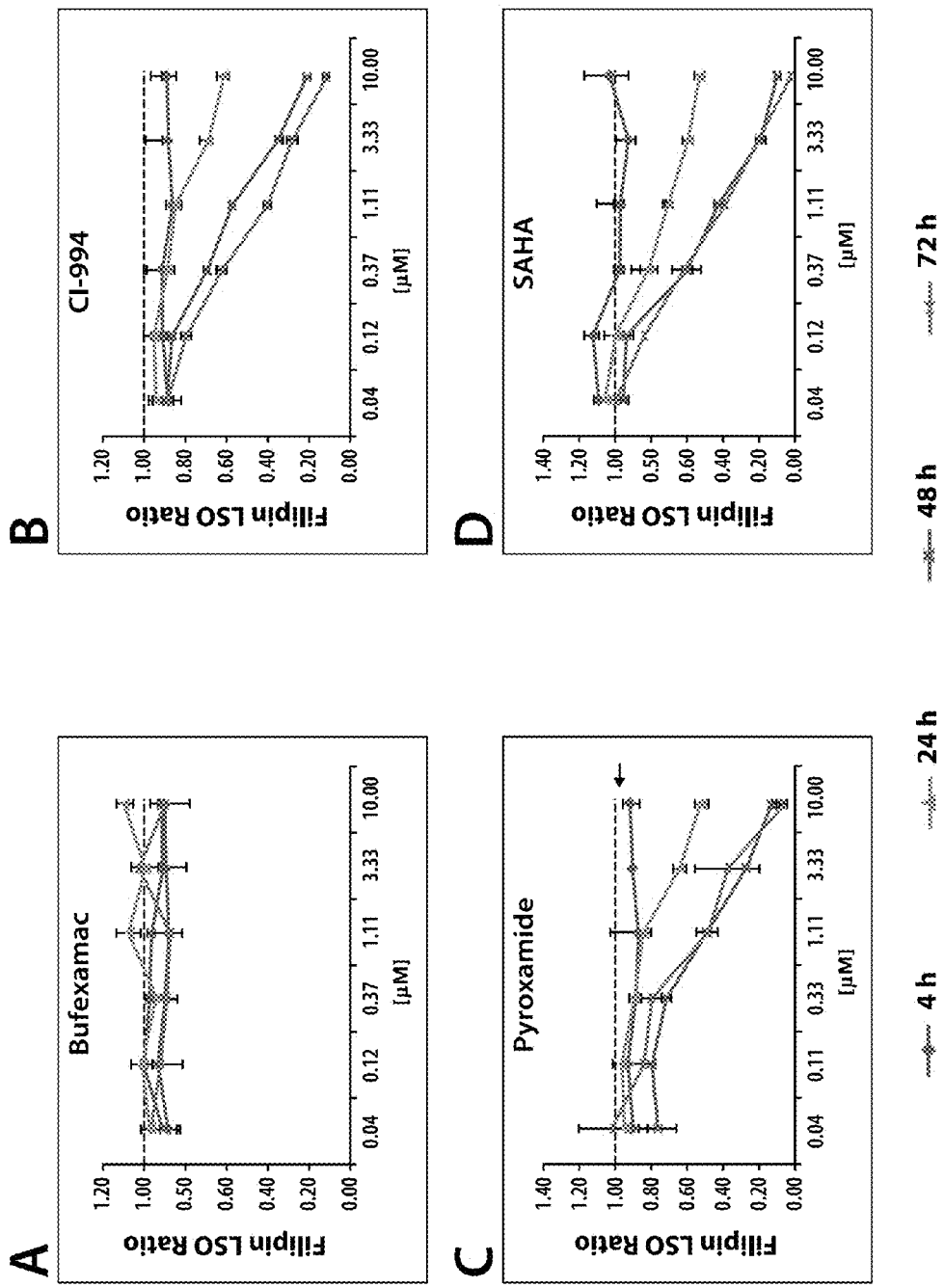
FIGS. 3A-3F illustrate dose and time dependence plots for six different HDACi: Bufexamac (FIG. 3A), CI-994 (FIG. 3B), Pyroxamide (FIG. 3C), SAHA (FIG. 3D), LBH-589 (FIG. 3E), and TSA (FIG. 3F), in accordance with various embodiments.
Figure 3:
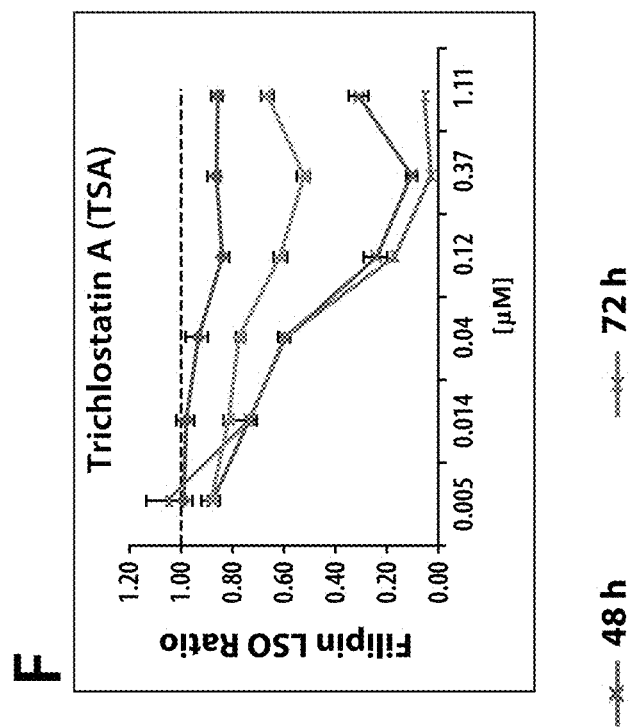
Figure 3:
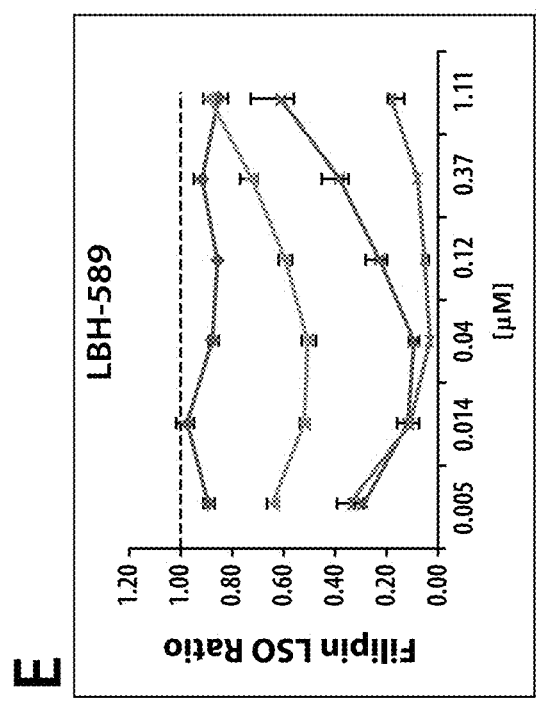

The effect of each HDACi on NPC1 human fibroblasts was then determined at varying concentrations and times. FIG. 3 shows the effects of four HDACi (CL-994, SAHA, LBH-589, and TSA) at different μM concentrations after 4, 24, 48 and 72 hours. Briefly, NPC1 human fibroblast GM03123 cells were seeded in five 384-well plates in growth medium. HDACi were added to achieve the final concentrations of 0.04 μM, 0.12 μM, 0.37 μM, 1.11 μM, 3.33 μM, and 10 μM. Due to high potency, two HDACi (LBH-589 and TSA) were treated with the lower concentration ranges of 0.0041 μM, 0.012 μM, 0.037 μM, 0.11 μM, 0.33 μM, and 1.11 μM. HDACi were allowed to remain in the culture medium for 72, 48, 24, 4, and 0 hours of treatment. For the control, cells were treated with a corresponding concentration of dimethyl sulfoxide (DMSO). HDACi were added to five wells for each concentration. Finally, cells were washed with phosphate-buffered saline (PBS), fixed with 2% paraformaldehyde (PFA), and stained with 50 μg/mL filipin before acquiring images for four sites/well using an ImageXpressMicro automated wide-field microscope at 10× magnification and 360/40 nm excitation/480/40 nm emission filters equipped with a 365 DCLP filter. Images were analyzed to obtain an LSO ratio and data were normalized to corresponding DMSO-treated cells. Data shown in FIG. 3 represent averages of three independent experiments totaling 60 images (5 wells×4 sites×3 experiments). The dotted horizontal lines indicate mean values for the solvent control, and error bars represent the standard error. Bufexamac treatment at various concentrations and times showed no correction of the NPC1 phenotype.

Although the treatment of NPC1 fibroblasts with CL-994 and SAHA showed no effect after 4 hours, within 24 hours significant correction of the NPC1 phenotype was observed at concentrations above 1.11 μM. LBH-589 was the most potent compound, and it corrected the NPC1 phenotype to near normal within 48 hours at 37 nM with a partial effect at 4 nM. TSA required about 10-fold higher concentration than LBH-589 to achieve the same level of correction.

In summary, as demonstrated herein, several HDACi showed efficacy in correcting the NPC1 phenotype, and LBH-589 was observed to be the most potent inhibitor. After 48 hours, the EC50 for CL-994, pyroxamide, and SAHA treatment was about 1 μM, for TSA the EC50 was about 20 nM, and for LBH-589 the EC50 was less than 4 nM.

Figure 4:
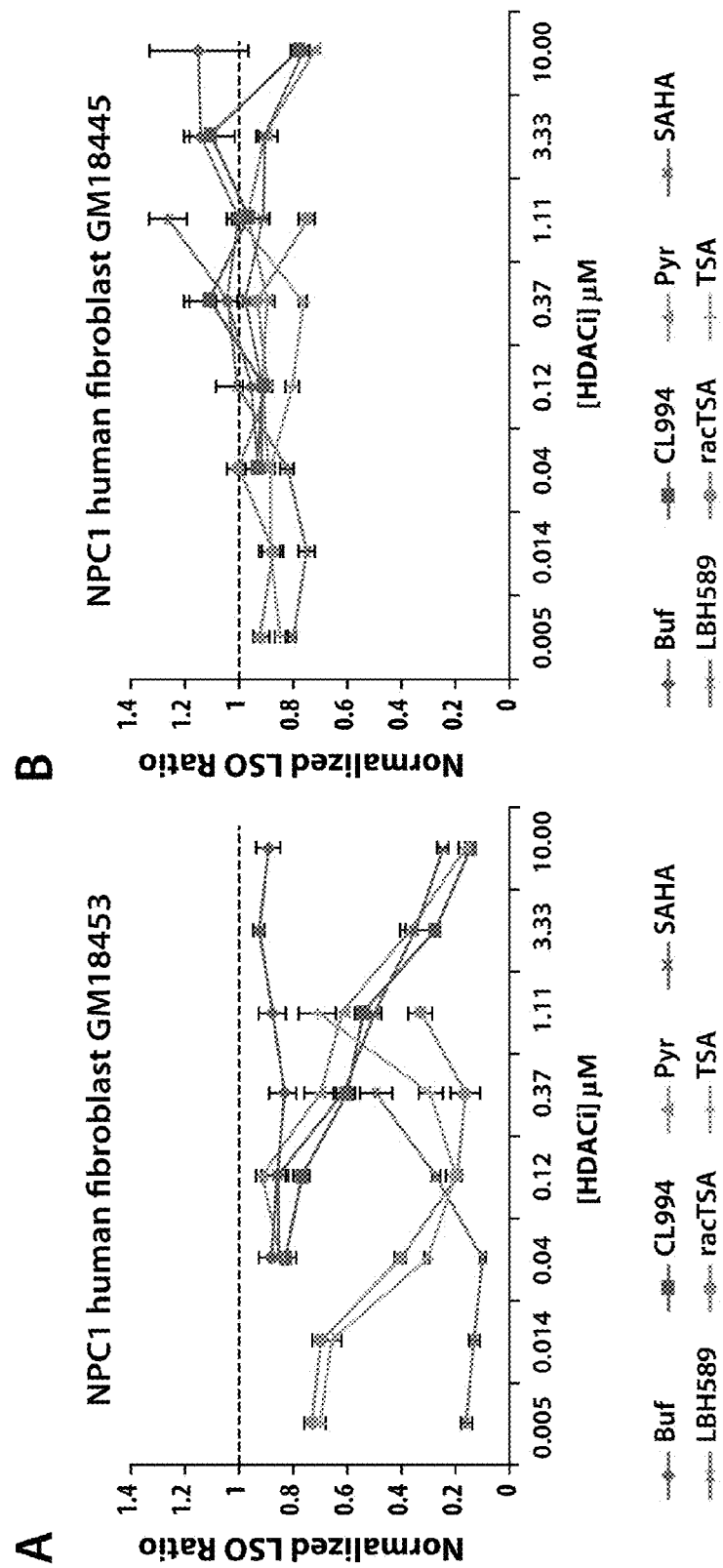
FIGS. 4A and 4B show dose dependence plots for NPC1 GM18453 cells (FIG. 4A) and NPC2 GM18455 cells (FIG. 4B) in the presence of the HDACi shown in FIGS. 3A-3F, in accordance with various embodiments.

Next, the effect of HDACi on NPC1I1061T homozygous NPC1 human fibroblasts (GM18453) and on NPC2 human fibroblasts (GM18445) was evaluated. Briefly, NPC1 human fibroblast GM18453 cells and NPC2 human fibroblast GM18455 cells were seeded in five 384-well plates in growth medium. HDACi were added 24 hours post plating to achieve the final concentrations of 0.04 μM, 0.12 μM, 0.37 μM, 1.11 μM, 3.33 μM, and 10 μM for four of the above mentioned HDACi (bufexamac, CL-994, pyroxamide, and SAHA). Due to high potency, the remaining three HDACi (LBH-589, TSA, and racemic TSA) were treated with the lower concentration range of 0.0041 μM, 0.012 μM, 0.037 μM, 0.11 μM, 0.33 μM, and 1.11 μM. For the control, cells were treated with a corresponding concentration of DMSO. HDACi were added to 5 wells for each concentration. Cells were incubated at 37° C. in the presence of 5% $CO_2$ atmosphere for 48 hours. Finally, cells were washed with PBS, fixed with 2% PFA, and stained with 50 μg/mL filipin before acquiring images for four sites/well using an ImageXpressMicro automated wide-field microscope at 10× magnification with 360/40 nm excitation and 480/40 nm emission filters equipped with a 365 DCLP filter. Images were analyzed to obtain an LSO ratio and data were normalized to corresponding DMSO-treated cells. Data shown in FIG. 4 represent averages of three independent experiments totaling 60 images (5 wells, 4 sites, 3 experiments). The dotted horizontal lines indicate mean values for the solvent control, and error bars represent the standard error.

FIG. 4A illustrates the dose-dependence for a 48-hour treatment with seven HDACi on NPC1 human fibroblast line GM18453 using the filipin assay. As was found with HDAC1 and GM03123, significant correction of the NPC1 phenotype was observed in GM18453 NPC1 cells. LBH-589 was quite effective in correcting the NPC1 phenotype at 4 nM, with the highest efficacy at 37 nM, followed by TSA at 111 nM. CL-994 and SAHA also caused improvement in the phenotype at concentrations above 333 nM.

FIG. 4B illustrates the free cholesterol content in LSOs of NPC2 fibroblasts determined by filipin staining 48 hours after HDACi treatment. None of the four HDACi tested was effective in significantly correcting the NPC phenotype in NPC2 cells.

Figure 5:
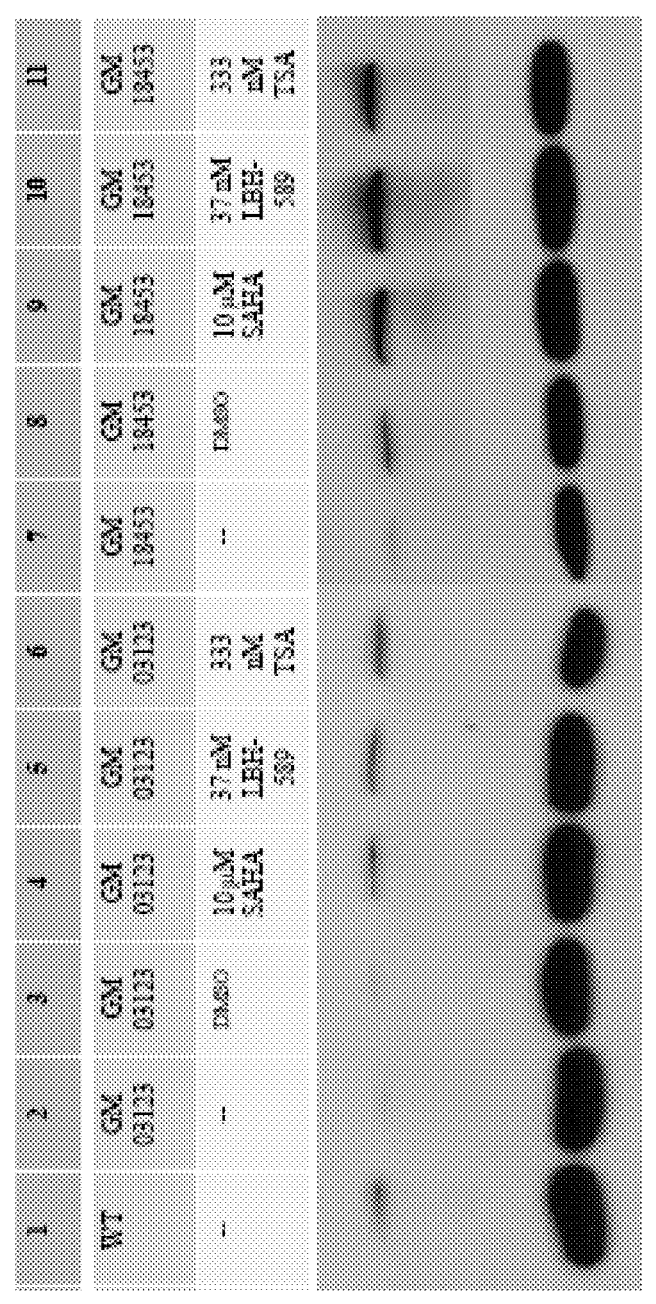

Without being bound by theory, it is believed that the mechanism of restoration of cholesterol homeostasis by HDACi is to modulate NPC1 levels. Thus, as illustrated in FIG. 5, protein expression levels were measured after treatment with three HDACi (SAHA, LBH-589 and TSA) at their respective optimum concentrations. Briefly, WT human fibroblast GM5659 cells, NPC1 human fibroblast GM03123 cells, and GM18453 cells were plated in 6-well plates. Cells were treated with either 37 nM LBH-589, 333 nM TSA, or 10 μM SAHA. As a control, cells were treated with DMSO. After 48 hours of incubation, cells were washed with PBS and lysed with lysis buffer for Western blot analysis. The membrane was probed with mouse monoclonal antihuman NPC1 antibody (Invitrogen), and anti-α-actin was used as a loading control. NPC1 protein expression was increased after HDACi treatment to levels comparable to the expression of NPC1 in WT cells. Thus, without being bound by theory, the correction of the NPC1 phenotype after HDACi treatment may be attributed to the increased levels of NPC1 protein.

Figure 6:
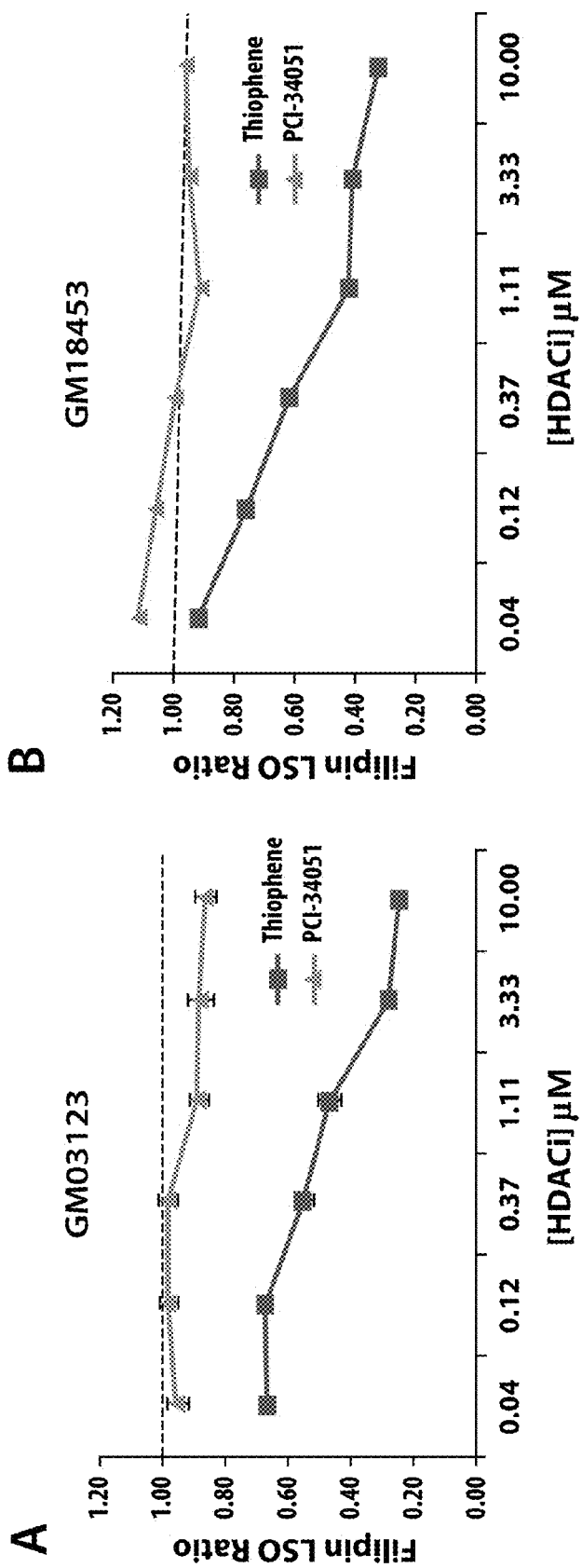
FIGS. 6A and 6B show dose dependence plots for NPC1 human fibroblast GM18453 cells (FIG. 6A) and NPC2 human fibroblast GM18455 cells (FIG. 6B) in the presence of isoform-specific HDACi, in accordance with various embodiments.

To further elucidate the mechanism of action, it was determined which particular HDAC classes and isoforms are responsible for the observed effect. It has been demonstrated previously that hydroxamic acids and benzamides are relatively weak inhibitors of class IIA HDACs. LBH-589, the most potent compound in the assay described above, has a Ki of 1 nM toward (class I) HDAC1, but 4.5 μM for (class IIa) HDAC7. Two known isoform-selective inhibitors, PCI-34051, a (class I) HDAC8-selective inhibitor, and thiophene benzamide, a (class I) HDAC1/2-selective inhibitor, were evaluated for their effect on two NPC1 human fibroblast lines, GM03123 and GM18453. Briefly, NPC1 human fibroblast GM18453 cells and NPC2 human fibroblast GM18455 cells were seeded in five 384-well plates in growth medium. Isoform-specific HDACi Bufexecap (Class IIb-specific), thiophene benzamide (class I-specific), and PCI-34051 (class I-specific), were added 24 hours post plating to achieve the final concentrations of 0.04 μM, 0.11 μM, 0.33 μM, 1.11 μM, 3.33 μM, and 10 μM. For controls, cells were treated with a corresponding concentration of DMSO. HDACi were added to 5 wells for each concentration. Cells were incubated at 37° C. in the presence of 5% $CO_2$ atmosphere for 48 hours. Finally, cells were washed with PBS, fixed with 2% PFA, and stained with 50 μg/mL filipin before acquiring images for four sites/well using an ImageXpressMicro automated wide-field microscope at 10× magnification, and 360/40 nm excitation and 480/40 nm emission filters equipped with a 365 DCLP filter. Images were analyzed to obtain an LSO ratio, and data were normalized to corresponding DMSO-treated cells. Data shown in FIG. 6 represent averages of three independent experiments totaling 60 images (5 wells, 4 sites, 3 experiments). The dotted horizontal lines indicate mean values for the solvent control, and the error bars represent the standard error.

As shown in FIG. 6, there was no correction of the NPC1 phenotype by the (class 1) HDAC8-selective inhibitor, PCI-34051, in the 40 nM to 10 μM concentration range. In contrast, treatment with the (class I) HDAC1/2-selective inhibitor thiophene benzamide resulted in significant reduction of cholesterol accumulation in LSOs of the NPC1 human fibroblasts. The correction was approximately 25% at 40 nM, but leveled off at approximately 80% at 3.33 μM and above in GM03123 cells. Thus, isoform HDAC8 is not the relevant target of less selective HDACi, yet HDAC1/2/3 inhibition may reduce the NPC phenotype.

Next, the involvement of HDAC6, the best characterized class IIB HDAC, was tested. Although the HDAC6-selective inhibitor tubacin has been described in the literature, with a Ki of 16 nM it is reasonably potent, but has only a 2-5:1 selectivity for class IIb over class I HDACs. Therefore, gene silencing was used to reduce expression of HDAC6 in GM03123 cells using siRNA.

Figure 7:
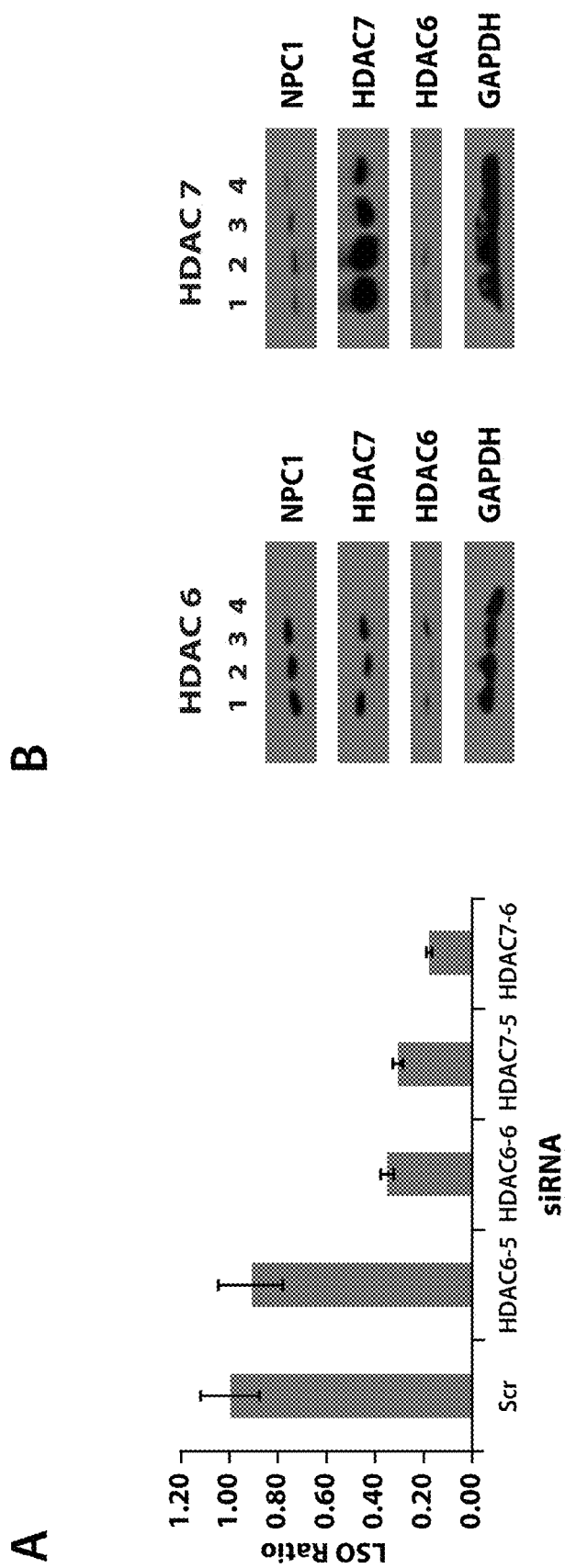
FIGS. 7A and 7B are a plot (FIG. 7A) and a Western blot (FIG. 7B) illustrating HDAC6 and HDAC7A silencing, in accordance with various embodiments.

Briefly, siRNA targeting class IIB HDAC6 or HDAC7A genes were transfected by electroporation in NPC1 human fibroblast GM03123 cells and plated either in poly-D-lysine (PDL)-coated cover-slip dishes for microscopy or in 6-well plates for Western blot analysis. The cells in PDL-coated dishes were washed with PBS, fixed with 2% PFA, and stained with filipin for microscopy. Images were acquired using wide-field microscopy and analyzed to estimate free cholesterol in LSO. Scrambled non-targeting siRNA was used as a control, and data were normalized to the control. The Western blot probed with mouse monoclonal anti-HDAC7A and anti-HDAC6 shown in FIG. 7B indicated that there was about a 50% reduction in HDAC7 protein or the HDAC6 protein, respectively, for HDAC7A and HDAC6 silenced NPC1 human fibroblasts GM03123. The quantification of LSO cholesterol (FIG. 7A) indicated that HDAC7A silencing resulted in 70-80% reduction in cholesterol accumulation, whereas HDAC6 silencing had no effect on cholesterol accumulation.

For reference, the inhibition constants Ki [μM] for several HDACi against HDAC 1-9 are shown below in Table 3.

TABLE 3

Inhibition Constants Ki [μM] for HDACi against HDAC 1-9

| Compound | HDAC1 | HDAC2 | HDAC3 | HDAC4 | HDAC5 | HDAC6 | HDAC7 | HDAC8 | HDAC9 |
|---|---|---|---|---|---|---|---|---|---|
| Bufexamac | | | | | | | | | |
| CL-994 | 0.05 | 0.19 | 0.55 | — | — | — | — | — | — |
| Pyroxamide | 0.0027 | 0.0036 | 0.008 | — | 4.75 | 0.0048 | — | 1 | — |
| SAHA | 0.0013 | 0.0016 | 0.005 | — | 3.6 | 0.0016 | — | 0.48 | — |
| TSA | 0.0002 | 0.00065 | 0.005 | 1.4 | 0.26 | 0.001 | 0.195 | 0.045 | 0.8 |
| LBH-589 | 0.001 | 0.00065 | 0.0011 | 0.55 | 0.08 | 0.0015 | 4.55 | 0.105 | 3.2 |
| Thio. Benzam. | 0.007 | 0.049 | 10 | >10 | >10 | >10 | >10 | >10 | — |
| PCI-34051 | 4.0 | >50 | >50 | — | — | 2.9 | — | 0.01 | — |

Thus, treatment of NPC1 human fibroblasts with nM concentrations of HDACi specific for class 1 HDACs not only clears the cholesterol accumulation due to mutated NPC1, but also increases the levels of the NPC1 protein. FIGS. 2 and 3 demonstrate that HDACi treatment leads to a near complete clearance of free cholesterol accumulation in NPC1 fibroblasts to a level comparable to untreated WT cells.

Figure 8:
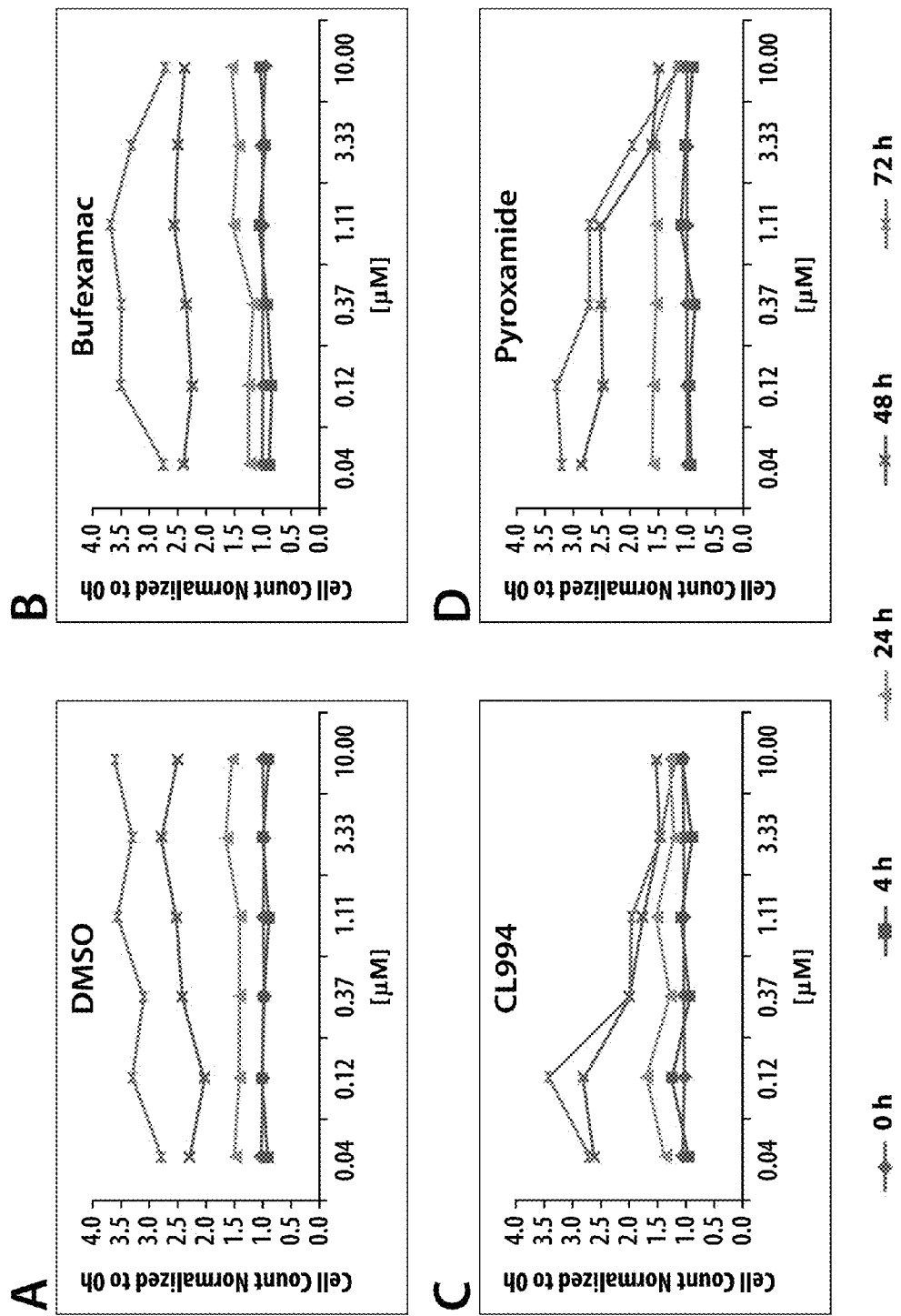
FIG. 8 illustrates results of a cell proliferation assay, in accordance with various embodiments.
Figure 8:
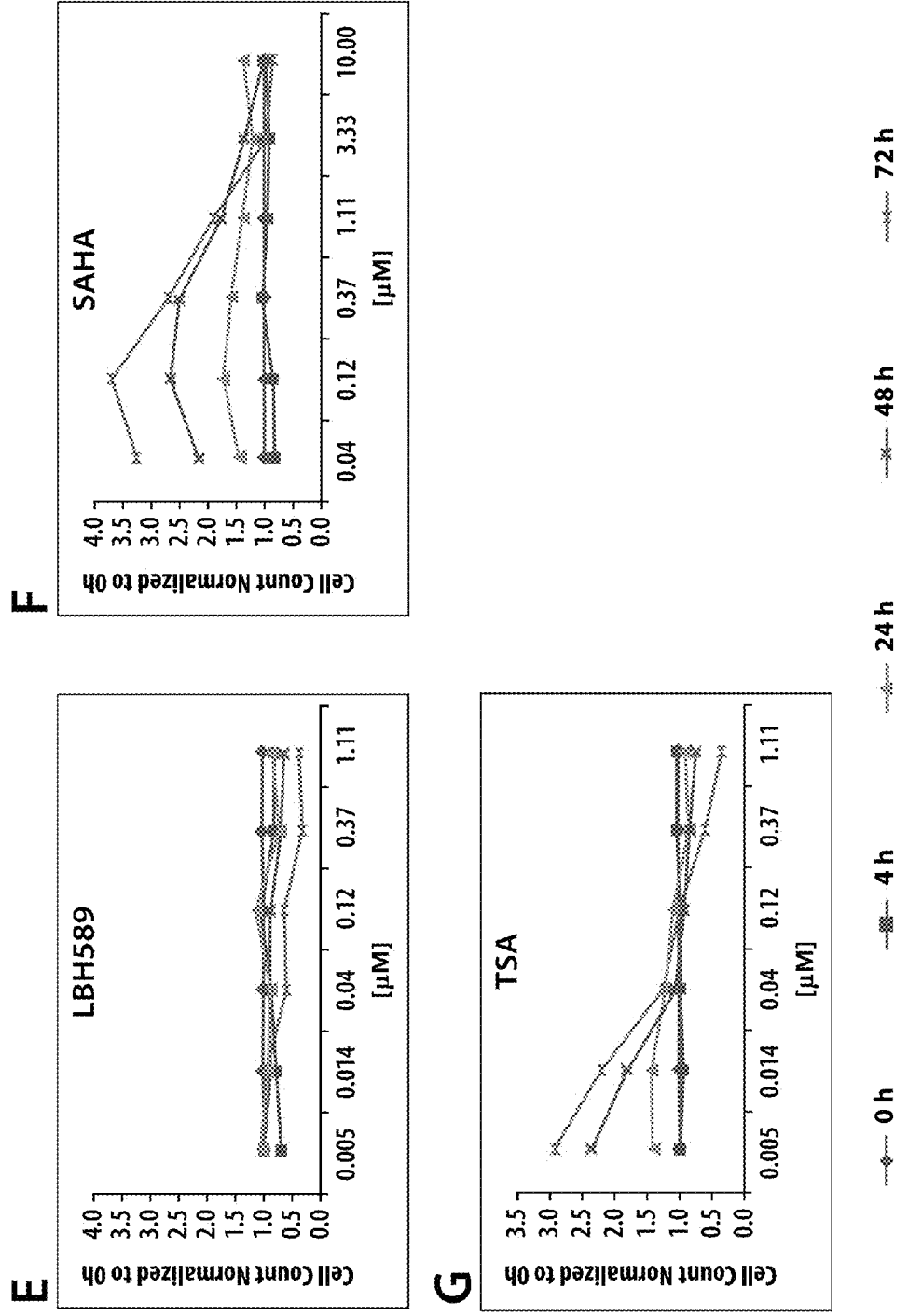
Figure 9:
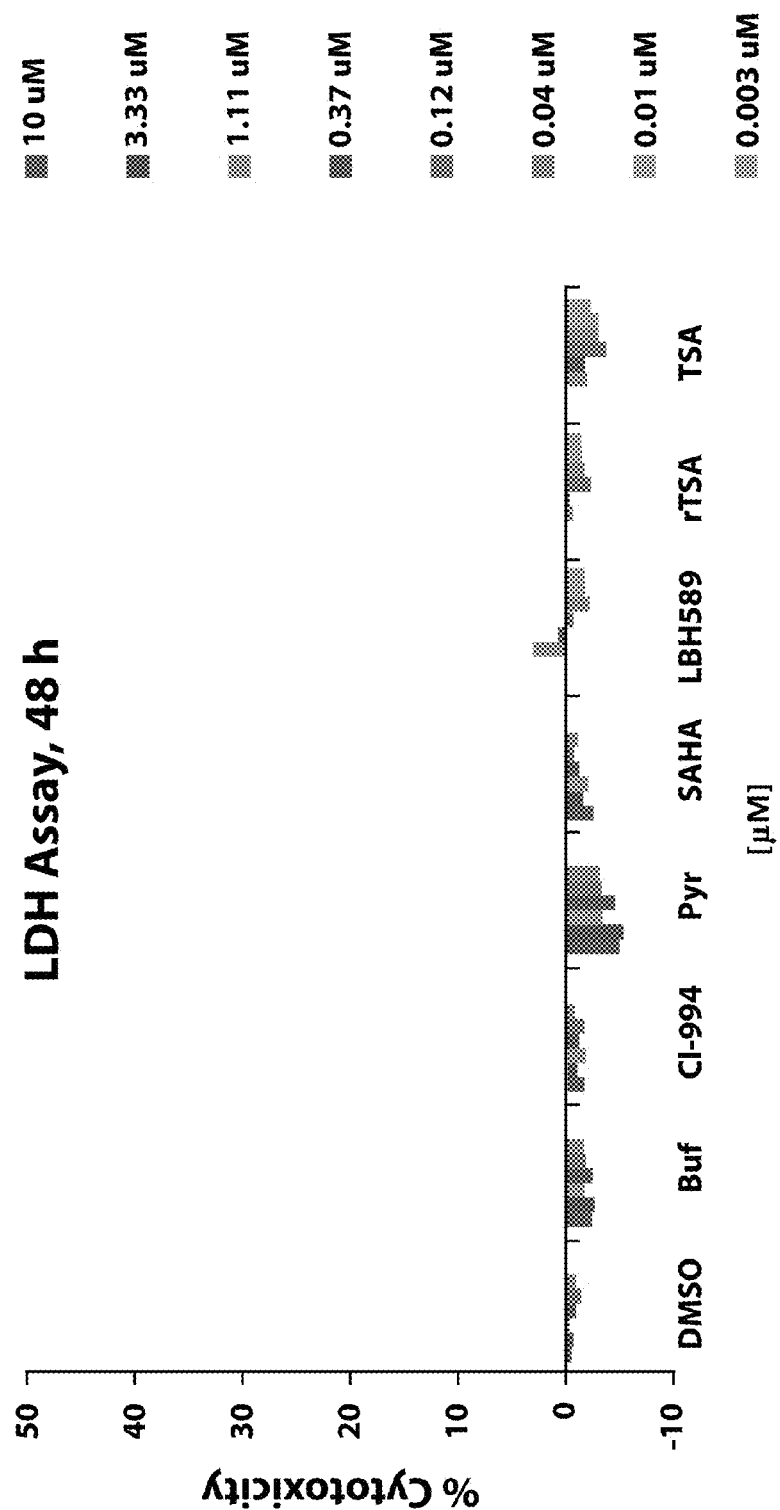
FIG. 9 illustrates results of a cytotoxicity assay, in accordance with various embodiments.

As shown in FIGS. 8 and 9, cell proliferation studies and cytotoxicity studies indicate that the compounds are cytostatic and not cytotoxic at the concentrations used. Briefly, for the cell proliferation assay shown in FIG. 8, HDAC inhibitors CL-995, SAHA, LBH-589, and TSA were added to NPC1 fibroblast GM03123 cells plated in 384-well plates at 0.04 μM, 0.12 μM, 0.37 μM, 1.11 μM, 3.33 μM, and 10 μM concentrations in quadruplicate. The cells were treated with HDACi on day 2 after seeding. The final DMSO concentration in each well, including control wells, was 0.2% v/v. The cells were incubated for 4, 24, 48 and 72 hours, respectively. At the end of each time period, cells were washed with PBS, fixed with 1.5% PFA, and washed with PBS again. Nuclei were stained using 2 nM Draq5 (5 μM stock solution in water) in PBS for 45 minutes at room temperature. Images were acquired using a Nikon 10× Plan Fluor NA objective and Cy5 filter set. One 696×520 pixel image was collected per well at 12 intensity bits per pixel. Each pixel was 3.125×3.125 μM in the object. Cells were counted by using "Count Nuclei" function of MetaXpress image analysis software. The number of standard areas per object above a threshold was determined, and the total number of standard areas per image was used as the cell count. The percent reduction in the number of cells compared to the DMSO control was calculated for each concentration and time.

For the LDH cytotoxicity assay shown in FIG. 9, the cytotoxicity of hit compounds was measured by an LDH release assay kit according to the manufacturer's instructions (Roche Diagnostic GmbH, Penzberg, Germany). Briefly, CT60 cells were plated in 96-well plates (Costar, Corning Inc., Corning, N.Y.) at a density of 3500 cells/well and incubated for 24 hours. Compounds were added to the CT60 cells at 0 μM (DMSO solvent control), 5 μM, 10 μM, and 20 μM concentrations in triplicate using methods similar to the dose-dependence assay described above. After 24 hours of treatment, 100 μl of tissue culture supernatant was removed, and LDH activity was determined by measuring absorbance at 492 nm using a SpectraMax M2 fluorescence plate reader (Molecular Devices Inc., Sunnyvale, Calif.). The experiment was repeated three times, so an average of nine data points is shown.

These results agree with published cytotoxicity data. The most potent compound described herein, LBH-589 or panobinostat, is currently being used in at least 60 clinical trials for various forms of cancer, including phase III trials. It is orally available, has good pharmacokinetic properties, and was demonstrated to have fewer of the cardiac side effects observed with many other HDACi. Thus, it is expected to be well-tolerated as a LSD therapeutic, for instance, for the treatment of NPC.

Thus, in various embodiments, HDAC inhibitors, particularly those that specifically target class I HDACs, may be useful for treating (for instance, ameliorating) a LSD such as NPC in a subject. In various embodiments, an HDACi that specifically targets class I HDACs may have a Ki for class I HDACs (or a class I HDAC isoform) that is lower than its Ki for class II, III, and/or IV HDAC (or class II, III, and/or IV HDAC isoforms). For instance, in some embodiments, an HDACi that specifically targets class I HDACs may have a Ki for class I HDACs (or one or more class I HDAC isoforms) in range of about 1,000 nM, or lower. For instance, an HDACi that specifically targets class I HDACs may have a Ki for class I HDACs (or a class I HDAC isoform) of less than 1,000 nM, for instance, about 750 nM, about 500 nM, about 250 nM, about 100 nM, about 50 nM, about 10 nM, about 1 nM, or even less. Conversely, an HDACi that does not specifically target class I HDACs may have a Ki for class I HDACs (or a class I HDAC isoform) of about 10 μM or higher. In particular embodiments, an HDACi that specifically targets class I HDACs may have a Ki for class I HDACs (or a class I HDAC isoform) of about 1,000 nM or lower, and a Ki for class II, III, and/or IV HDACs (or a class II, III, and/or IV HDAC isoform) of about 10 μM or higher.

In other embodiments, an HDACi that specifically targets class I HDACs may inhibit class I HDACs (or a class I HDAC isoform) more effectively than it inhibits class II, III, and/or IV HDACs (or class II, III, and/or IV HDAC isoforms). For instance, an HDACi that specifically targets class I HDACs (or a class I HDAC isoform) may exhibit about 3×, 4×, 5×, or 10× (or even more) inhibition of a class I HDAC (or a class I HDAC isoform) than it exhibits for class II, III, and/or IV HDACs.

In still other embodiments, an HDACi that specifically targets class I HDACs may inhibit approximately 70%, 80%, 90%, or 100% of an activity of a class I HDAC (or a class I HDAC isoform), yet it may inhibit less than about 50%, 40%, 30% 20%, or 10% of an activity of a class II, III, and/or IV HDAC (or class II, III, and/or IV HDAC isoform).

Specific, non-limiting examples of HDACi that specifically target class I HDACs include trichostatin A, trichostatin A derivatives, givinostat (ITF2357), and LBH -589 (panobinostat).

In another embodiment, a method for treating an LSD, such as NPC, in a subject is provided. The method includes selecting a subject having an LSD, and administering to the subject a therapeutically effective dose of a class I-specific HDACi. In particular embodiments, the method includes selecting a subject having NPC, and administering to the subject a therapeutically effective dose of a class I-specific HDACi. Although class I-specific HDACi may be used to treat a wide variety of LSDs in animal and human subjects, they may be particularly effective at treating NPC.

As used herein, the term "treat" or "treatment" is used to refer to any therapy that reduces or ameliorates a symptom of a disease or disorder, such as a reduction of an abnormal accumulation of unesterified cholesterol, glycosphingolipids, bis(monoacyl glycerol) phosphate, or other lipids in late endosome/lysosomes, such as is characteristic of some LSDs. As used herein, the term "treatment" may refer a therapy that causes a cure or reduction of a symptom to a normal state or condition, or it may refer to a therapy that causes only a partial reduction in a symptom, such as a 10%, 20%, 30%, 40%, 50%, 60%, 70%, 80%, or 90% reduction.

As used herein, the term "therapeutically effective amount" includes a quantity of a specified compound (such as a class I-specific HDACi, for instance trichostatin A, a trichostatin A derivative, givinostat (ITF2357), or LBH-589 (Panobinostat)) required to achieve a desired effect in a subject being treated. For instance, this may be the amount necessary to treat an LSD, such as NPC, or a dose sufficient to prevent advancement, or to cause regression of an LSD, such as NPC, or which is capable of reducing the amount of unesterified cholesterol, glycosphingolipid, or bis(monoacyl glycerol) phosphate that may be stored in late endosome/lysosomes (LE/Ly).

Various dosage ranges and administration schedules may be adopted for therapeutic treatment of LSDs, such as NPC, in animal and human subjects with the class I-specific HDACi as disclosed herein. In an embodiment, such a therapeutically effective amount of a class I-specific HDACi may be in the range of about 0.1 to about 100 mg/kg, or in some embodiments, from about 3.0 to about 50 mg/kg, of body weight/day. Such dosages may vary depending upon the age and requirements of the patient, the severity and type of LSD being treated, and the particular class I-specific HDACi being used. In some embodiments, the class I-specific HDACi may be administered in conjunction with one or more other class I-specific HDACi, or other therapeutic agents, for instance, a cyclodextrin, Zavesca (Miglustat), or 5-aza-2'-deoxycytidine (5azaD).

In some embodiments, the class I-specific HDACi (for instance, trichostatin A, trichostatin A derivative, or LBH-589 (Panobinostat)) may be administered systemically, whereas in other embodiments the class I-specific HDACi may be administered locally. An effective dose of a disclosed class I-specific HDACi may be administered systemically in a variety of ways. For instance, systemic administration may be oral, or by injection, for instance intravenous, intra-arterial, subcutaneous, intramuscular, intrathecal, or intra-peritoneal injection. Systemic administration also may include transdermal or inhalational administration.

An effective amount of a class I-specific HDACi may be administered in a single dose, or in multiple doses, for example daily, or every four, eight, or twelve hours, during a course of treatment (for instance, during chronic treatment). In one embodiment, a therapeutically effective amount of a class I-specific HDACi may be administered as a single pulse dose, as a bolus dose, or as pulse doses administered over time. In specific, non-limiting examples, pulse doses of a class I-specific HDACi may be administered during the course of a day, during the course of a week, or during the course of a month. In some embodiments, the class I-specific HDACi may be administered to the subject on a schedule that includes several daily doses of the class I-specific HDACi, followed by a withdrawal period, for example to reduce toxicity. This dosage pattern may be repeated until the desired therapeutic effect is achieved, for example reducing the amount of unesterified cholesterol, glycosphingolipid, or bis (monoacyl glycerol) phosphate that are stored in late endosome/lysosomes (LE/Ly). Once the desired therapeutic effect is achieved, this dosage pattern may be maintained, or a maintenance dosage pattern may be employed.

In some embodiments, the class I-specific HDACi may be administered locally. In certain embodiments, this may be accomplished by local injection into the body part that is particularly affected by the LSD, for example by injecting or infusing the class I-specific HDACi directly into the CSF or brain of a subject with NPC (for instance, intrathecally). In other embodiments, local administration may be accomplished by implanting a sustained-release device such as a pump or a micropump, or sustained-release implant, such as a bead or gel that contains the class I-specific HDACi and slowly releases the drug into the desired area over time.

In another embodiment, the class I-specific HDACi may be incorporated into a pharmaceutical composition. In cases where class I-specific HDACi are sufficiently basic or acidic to form stable nontoxic acid or base salts, use of the compounds as pharmaceutically acceptable salts may be appropriate. Examples of pharmaceutically acceptable salts within the scope of embodiments of the present disclosure include organic acid addition salts formed with acids which form a physiological acceptable anion and inorganic salts.

Pharmaceutical compositions in accordance with embodiments of the disclosure may be prepared by combining the class I-specific HDACi with a solid or liquid pharmaceutically acceptable carrier and, optionally, with pharmaceutically acceptable adjuvants and excipients employing standard and conventional techniques. Solid form compositions include, for instance, powders, tablets, dispersible granules, capsules, cachets, and suppositories. A solid carrier may be at least one substance that may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the class I-specific HDACi dissolved in water and water-propylene glycol systems, optionally containing suitable conventional coloring agents, flavoring agents, stabilizers, and/or thickening agents.

In an embodiment, a pharmaceutical composition may be provided employing conventional techniques in unit dosage form containing effective or appropriate amounts of one or more active component. In embodiments, the quantity of active component (e.g., class I-specific HDACi) in a pharmaceutical composition and unit dosage form thereof may be varied or adjusted widely depending upon the particular application, the potency of the particular compound and the desired concentration. In an embodiment, the quantity of active component may range from 0.5% to 90% by weight of the composition.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A method of increasing a level of NPC1 protein in a cell, comprising:
    selecting a cell having a mutant NPC1 gene or expressing a mutant NPC1 protein; and
    contacting the cell with an effective amount of a class I-specific histone deacetylase inhibitor, thereby increasing the level of NPC1 protein in the cell; wherein the class I-specific histone deacetylase inhibitor has a Ki of less than 1 µM for at least one class I histone deacetylase; and wherein the class I-specific histone deacetylase inhibitor is selected from the group consisting of trichostatin A, LBH-589(Panobinostat), and SAHA (Vorinostat).

2. The method of claim 1, wherein the cell is a human cell.

3. The method of claim 2, wherein the cell is from a human embryo, fetus, infant, child, or adult.

4. The method of claim 1, wherein the cell is in a human subject, and wherein the method further comprises administering to the subject a therapeutically effective dose of an additional compound effective for ameliorating Niemann-Pick type C disease.

5. The method of claim 4, wherein the additional compound is a second class I-specific histone deacetylase inhibitor.

6. The method of claim 4, wherein the additional compound is a cyclodextrin, Zavesca (Miglustat), or 5-aza-2'-deoxycytidine (5azaD).

7. The method of claim 1, wherein the cell is in a subject, and wherein the subject has Niemann-Pick type C disease.

8. The method of claim 7, wherein the cell is a human or animal cell, and wherein contacting the cell comprises contacting the cell in vivo in the human or animal.

9. The method of claim 8, wherein the human is an embryo, a fetus, an infant, a child, or an adult.

10. The method of claim 7, wherein the cell is a liver cell, a spleen cell, a lung cell, or a CNS cell.

* * * * *